(12) United States Patent
Klitgaard

(10) Patent No.: US 6,302,869 B1
(45) Date of Patent: *Oct. 16, 2001

(54) SYRINGE HAVING A FLEXIBLE PISTON ROD

(75) Inventor: Peter Christian Klitgaard, Smørum (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/887,763

(22) Filed: Jul. 3, 1997

(30) Foreign Application Priority Data

Jul. 5, 1996 (DK) .................................. 0757/96

(51) Int. Cl.[7] .................................. A61M 5/315
(52) U.S. Cl. .................................. 604/218; 604/209
(58) Field of Search .................................. 604/152, 4.01, 604/207–210, 218, 220, 181, 187, 224

(56) References Cited

U.S. PATENT DOCUMENTS

| 4,787,893 | * | 11/1988 | Villette | 604/154 |
| 4,846,797 | * | 7/1989 | Howson et al. | 604/154 |
| 4,908,017 | * | 3/1990 | Howson et al. | 604/154 |
| 5,304,152 | * | 4/1994 | Sams | 604/218 |
| 5,368,572 | * | 11/1994 | Shirota | 604/154 |
| 5,380,295 | * | 1/1995 | Vacca | 604/218 |
| 5,672,155 | * | 9/1997 | Riley et al. | 604/154 |

FOREIGN PATENT DOCUMENTS

WO 95/09021   4/1995   (WO) .

* cited by examiner

*Primary Examiner*—Anhtuan T. Nguyen
*Assistant Examiner*—Michael M Thompson
(74) *Attorney, Agent, or Firm*—Skadden, Arps, Slate, Meagher & Flam LLP

(57) ABSTRACT

A flexible piston rod for use in cylinder ampoules comprises a tape shaped body (1) which is along its length provided with supporters (2; 6; 16) projecting from at least one side of the tape. The tape (1) has a width and the supporters a length so that sides of the tape and the free ends of the supporters abuts the inner wall of the ampoule (3) in at least three positions along the inner perimeter of the ampoule (3) and not all the abutment points lies on the same half of the circular cross section but are typically displaced about 120° from each other. The piston rod is moved by a gear engaging a rack (12) on the tape either on the side not carrying supporters or at the edge of the tape on the side carrying supporters.

12 Claims, 1 Drawing Sheet

SYRINGE HAVING A FLEXIBLE PISTON ROD

CROSS-REFERENCE TO RELATED APPLICATIONS

Figure 1:
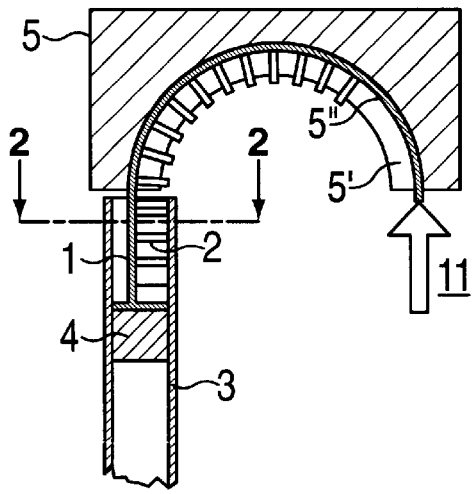

This application claims priority under 35 U.S.C. 119 of Danish application 0757/96 filed Jul. 5, 1996, the contents of which are fully incorporated herein by reference.

The invention relates to flexible piston rods for injection syringes.

Injection syringes are mainly provided with a rigid piston rod by which a piston is pressed into one end of a cartridge to press out the content of said cartridge through an injection needle mounted at the other end. Such injection syringes will mainly have a length which is at least twice the length of the cartridge.

To provide shorter syringes flexible piston rods have been proposed. As used in the specification and claims, the term "flexible piston rod" refers to a piston rod which may be deflected so that its; outer end lies parallel with the cartridge next to this cartridge and not in axial continuation thereof.

WO 95/09021 describes a flexible piston rod for a syringe comprising a cartridge holder and a dose setting part. Set doses are pressed out of the cartridge by a flexible piston rod which is deflected 180° by a piston rod guide placed immediately behind the cartridge. As the syringe is of the type in which an empty cartridge may be replaced by a new one after the piston rod has been retracted from the empty cartridge, the piston rod guide must be so designed that it can support the piston rod both when a pressure and a drag is transmitted through this piston rod. This is obtained by using a piston rod guide having the shape of a curved tube supporting all sides of the piston rod which is made as a tight wound steel spring.

For use in a disposable syringe with a flexible piston rod the piston rod guide only have to support the piston rod during its transmission of pressure to a piston in the cartridge and consequently a more simple piston rod guide may be used. Further it is wanted to manufacture the piston rod from a material of the same kind as the material from which the disposable syringe is made, i.e. plastic as combination of metal parts and plastic parts reduces the recycling possibilities. Also the piston rod shall compromise between the need for a piston rod which is sufficiently rigid to not bend out and the wish for a minimised consumption of material.

From EP 110 687 it is known to use a flexible pusher tape to drive a piston into a cartridge. The tape is made of a plastic such as moulded polypropylene and the needed stiffness is obtained by giving the tape a curved cross section and by beads along the lateral edges of the tape. The curved shape of the cross section corresponds to the curving of the inner wall of the cartridge so that the tape may abut this inner wall in its full width.

However, when a tape with a curved cross section is deflected to follow an arc of a circle, the tape have to assume a linear cross section. Furthermore plastic possesses a memory so that a cross section which has for some time been kept linear will not automatically attain the original curved shape when the part in question is no longer following an arc of a circle. Consequently a cross section which is intended to follow the curve shape of the inner wall of a cartridge cannot be relied on.

It is the object of the invention to provide a flexible piston rod made of plastic and which may be deflected outside a cartridge and used for pressing a piston into a cartridge without bending out within this cartridge.

This is obtained by a piston rod which comprises a tape shaped body which is along its length provided with supporters projecting from at least one side of the tape, the tape having a width and the supporters a length so that the sides of the tape and the ends of the supporters abuts the inner wall of an ampoule in at least three positions along the inner perimeter of the ampoule with not all the supporting points lying in the same half of the circular cross section.

In a preferred embodiment of a piston rod according to the invention the tape shaped body has a width corresponding to the length of a chord spanning an arc of about 120° of the circular inner cross section of the ampoule and supporters projecting perpendicularly from the side of the tape facing the axis of the ampoule abuts the inner wall of this ampoule in a position 120° displaced form each of the sides of the tape shaped body.

According to the invention the supporters may be provided with a spacing allowing the piston rod to be deflected to the side carrying the supporters. Supporters may be provided on both sides of the tape to enhanced the stiffness of the piston rod in the ampoule. By such piston rods the piston rod guide must be provided with a slot in the moving directions of the piston rod to accommodate projecting supporters.

Alternatively the supporters may be placed adjacent to each other so that the piston rod can only be deflected to the side away from the supporters. The piston rod guide must the be designed with a slot which may accommodate the projecting supporters.

In an embodiment of the piston rod according to the invention the supporters may have the shape of plates oriented in the longitudinal direction of the piston rod body perpendicular to this body and connected to the piston rod body by connections having a small length in the longitudinal direction of the piston rod. This construction possesses enhanced stiffness and as the connections of the plates to the piston rod is small, e.g. of the same order of size as is the thickness of the tape forming the piston rod, in the longitudinal direction of this rod they will not reduce the flexibility of this piston rod.

In another embodiment of the piston rod according to the invention this rod may be composed by tape shaped pieces each having a plate shaped supporter fixed to it along the whole length of the piece, the pieces being connected by hinges allowing deflection of the pieces to the side not carrying the supporters. In this embodiment the tape shaped pieces forming the piston rod has obtained a good stiffness on the account of the overall flexibility of the piston rod.

For the advancing of the piston rod according to the invention racks may be provided either on a side carrying no supporters or next to such supporters along the edge of the piston rod on the same side as these supporters. In embodiments with stiffened tape pieces the rack may be composed of sector shaped racks matching a drive pinion.

Figure 2:
Figure 3:
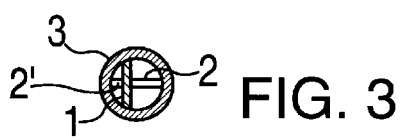
Figure 5:
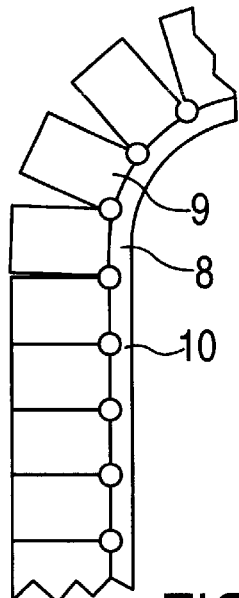
Figure 4:
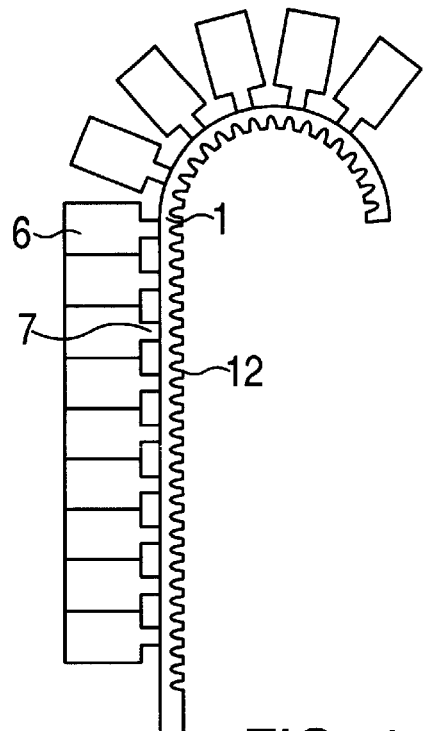
Figure 6:
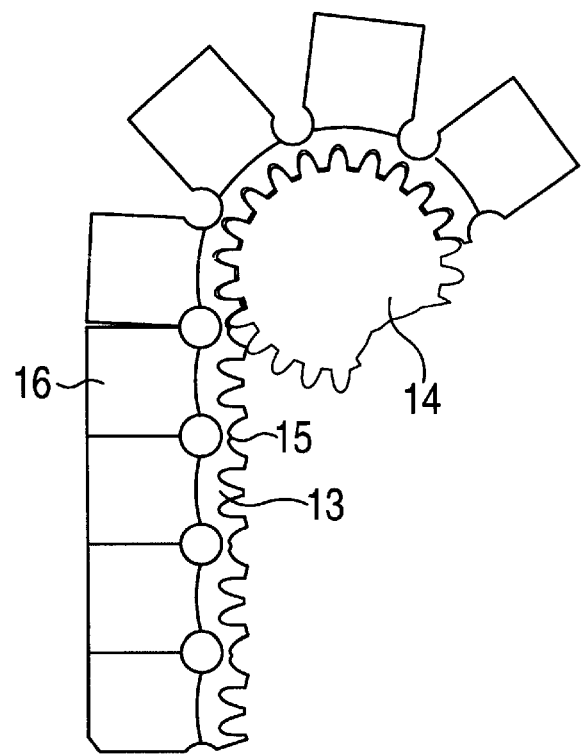

In the following the invention will be described in further details with references to the drawing wherein FIG. 1 shows a side view of an embodiment of a piston rod according to the invention inserted in an ampoule and deflected by a piston rod guide, FIG. 2 shows a sectional view along the line II—II in FIG. 1, FIG. 3 shows another embodiment of a deflected piston rod according to the invention, FIG. 4 shows still another embodiment of a deflected piston rod according to the invention, FIG. 5 shows a further embodiment of a piston rod according to the invention, and FIG. 6 shows still a further embodiment of a piston rod according to the invention.

In FIG. 1 a tape shaped piston rod 1 is along one of its sides provided with spaced supporters 2. The piston rod is shown inserted in an ampoule 3 and abutting a piston 4 in said ampoule. Immediately outside the ampoule the piston rod is deflected by a piston rod guide 5. The piston rod guide 5 has a curved surface supporting the convex side of the deflected piston rod. At its sides the piston rod guide 5 has flanges 5' each carrying another flange 5" parallel with the curved surface of the piston rod guide at a distance corresponding to the thickness of the tape forming the piston rod. This way a guide way is formed which prevents the piston rod from taking a short cut along a chord to the curved surface when no compressive forces act on the piston rod. FIG. 2 shows how the side edges of the tape shaped piston rod 1 and the ends of the supporters abuts the inner perimeter of the ampoule. The tape shaped piston rod abuts the inner perimeter of the ampoule so that the rectangular cross section of the tape forms a chord in the circular cross section of the ampoule. The supporters project perpendicular to the side of the tape facing the centre of the circular cross section of the ampoule to prevent bending out of the tape in this direction. Bending out in a direction away from the centre of the circular cross section is prevented by the fact that the tape have to attain a curved cross section to allow such a bending out. When the width of the tape is small the tape will posses a sufficient stiffness to avoid such a curving. However, in ampoules with a large diameter supporters on the side of the tape not facing the centre of the cross section of the ampoule may be appropriate as shown by the supporters 2' in FIG. 3.

In the embodiment shown in FIG. 1 the piston rod guide deflects the piston rod in the direction of the supporters. This will make the radius of curvature which can be allowed for the deflection dependent on the spacing between the supporters. In FIG. 4 is shown an embodiment of the piston rod in which embodiment the supporters abut each other when the piston rod is linear and not deflected. This gives the linear piston rod a good stiffness. The piston rod may be deflected by a not shown piston rod guide if only the deflection is made toward the side of the tape shaped piston rod which have no projecting supporters. The piston rod guide must be provided with a slot which can accommodate the supporters which now project from the side of the tape abutting the piston rod guide.

In the embodiments shown in FIG. 1 the supporters have only a small extension in the longitudinal direction of the piston rod if they shall not hamper the deflection of the piston rod. In the embodiment shown in FIG. 4 the supporters are formed as plate shaped members 6 which are connected to the piston rod 1 by connections 7 having only a small extension in the longitudinal direction of the piston rod.

In still another embodiment of the piston rod according to the invention is sketched in FIG. 5. The tape shaped piston rod is composed of pieces 8 of tape and each piece 8 has a longitudinal wall 9 projecting perpendicularly from one of its sides. The tape pieces 8 are hinged together by hinges 10 to form a piston rod which may only be deflected by bending in its hinges.

The piston rod may be advanced by adding pressure at its end outside the ampoule as shown by the arrow 11 in FIG. 1. Alternatively the piston rod may on its tape shaped body be provided with a flexible rack 12 as shown in FIG. 4 by which rack the piston rod is advanced by a pinion engaging said rack and being rotated in accordance with the requested advancing of the piston rod. The rack may either be provided on a side of the piston rod which does not carry supporters as shown in FIG. 4 or next to the supporters along the edges of the tape shaped piston rod body (not shown). Alternatively a perforation may be provided along the edge of the piston rod and the advancing of the piston rod may be obtained by sprocket wheels engaging said perforation.

When the piston rod is not overall flexible but is flexible only in hinges the parts between the hinges are rigid and not flexible, a rack on the side not carrying the supporters can be shaped as sectors of an inwardly toothed gear matching the outward toothed pinion which drives the piston rod as sketched in FIG. 6 wherein the rigid pieces 13 of the piston rod are provided with curved racks which are engaged by a pinion 14. On the piston rod side opposite the curved racks plate shaped supporters 16 are provided. The deflection of the piston rod is obtained by bending the piston rod in the hinges 15 connecting the rigid pieces forming the piston rod.

What is claimed is:

1. A syringe for receiving an ampoule having a cylindrical interior of a specified first diameter, said syringe comprising:
    a flexible piston rod having a tape-shaped body, said body including opposed top and bottom surfaces and opposed sides, wherein said piston rod further includes a plurality of support members spaced axially along said body and projecting from said top surface, wherein said support members have distal ends spaced away from said body, and wherein said sides and said distal ends, when said piston rod is viewed in cross-section, lie at least generally along a circle having a diameter which is approximately the same as said first diameter so that, when said piston rod extends into the cylindrical interior of an ampoule, the sides and distal ends will abut the ampoule interior at least at three contact positions, and wherein one of said contact positions is located on a half of said circle opposite to the other two contact positions; and
    a piston rod guide member for guiding a portion of said piston rod, which is located outside of an ampoule interior, along a curved guide surface.

2. A syringe according to claim 1, wherein said support members are axially spaced from one another to allow said piston rod to be deflected towards said support members.

3. A syringe according to claim 1, wherein said support members have axially spaced leading and trailing edges which abut one another when said piston rod is straight, such that said piston rod can be deflected only in a direction opposite to said support members.

4. A syringe according to claim 3, wherein said tape-shaped body comprises a plurality of tape-shaped pieces, each having a plate shaped supporter fixed to it along the whole length of said piece such that individual pieces are not flexible, the pieces being connected by hinges allowing said piston rod to deflect in a direction opposite to said support members.

5. A syringe according to claim 4, further comprising a pinion for driving said piston rod, and wherein said pieces, along said bottom surface, include sector shaped rack portions for engaging said pinion.

6. A syringe according to claim 3, wherein said support members include plate-shape portions which lie in a plane perpendicular to said top surface and parallel to said axis, and wherein said plate-shape portions are connected to said top surface by connecting portions having an axial dimension less than said plate-shape portions.

7. A syringe according to claim 1, comprising a rack along said bottom surface.

8. A syringe according to claim 1, comprising a rack along said top surface.

9. A syringe according to claim 1, comprising a plurality of axially spaced additional support members extending from said bottom surface and having distal ends lying along said circle.

10. A syringe according to claim 1, wherein said tape-shaped body has a cross-sectional width, defined as the distance between said opposed sides, corresponding to the length of a chord spanning an arc of said circle, and wherein said support members project perpendicular to said top surface.

11. A syringe according to claim 10, wherein said cross-sectional width corresponds to a chord spanning an arc of approximately 120 degrees.

12. A syringe according to claim 10, wherein said three contact positions are separated from one another along said circle by an angle of approximately 120°.

* * * * *